(12) United States Patent
Ogura et al.

(10) Patent No.: US 7,833,985 B2
(45) Date of Patent: Nov. 16, 2010

(54) ANGIOTENSIN-CONVERTING ENZYME INHIBITORY PEPTIDES

(75) Inventors: Kyoichi Ogura, Kyoto (JP); Taeko Iino, Otsu (JP); Sumio Asami, Ibaraki (JP)

(73) Assignee: Suntory Holdings Limited, Osaka-shi, Osaka (JP)

(*) Notice: Subject to any disclaimer, the term of this patent is extended or adjusted under 35 U.S.C. 154(b) by 642 days.

(21) Appl. No.: 10/549,176

(22) PCT Filed: Mar. 17, 2004

(86) PCT No.: PCT/JP2004/003588
§ 371 (c)(1),
(2), (4) Date: Aug. 14, 2006

(87) PCT Pub. No.: WO2004/082709
PCT Pub. Date: Sep. 30, 2004

(65) Prior Publication Data
US 2006/0276627 A1  Dec. 7, 2006

(30) Foreign Application Priority Data
Mar. 18, 2003 (JP) .............................. 2003-074488

(51) Int. Cl.
*A61K 38/06* (2006.01)
(52) U.S. Cl. ....................................................... 514/18
(58) Field of Classification Search ........................ None
See application file for complete search history.

(56) References Cited

U.S. PATENT DOCUMENTS

| | | | |
|---|---|---|---|
| 4,867,973 A * | 9/1989 | Goers et al. | 424/181.1 |
| 5,238,921 A | 8/1993 | Maruyama et al. | |
| 5,558,993 A * | 9/1996 | Champion et al. | 435/6 |
| 6,410,685 B1 | 6/2002 | Masuyama et al. | |
| 7,034,002 B1 | 4/2006 | Fujita | |

FOREIGN PATENT DOCUMENTS

| | | |
|---|---|---|
| EP | 0 445 606 | 9/1991 |
| EP | 1 018 341 | 7/2000 |
| EP | 1 092 724 | 4/2001 |
| JP | 52-148631 | 12/1977 |
| JP | 58-109425 | 6/1983 |
| JP | 59-44323 | 3/1984 |
| JP | 60-23086 | 6/1985 |
| JP | 60-23087 | 6/1985 |
| JP | 61-36226 | 2/1986 |
| JP | 61-36227 | 2/1986 |
| JP | 2-36127 | 2/1990 |
| JP | 02240028 * | 9/1990 |
| JP | 402240028 A | 9/1990 |
| JP | 3-11097 | 1/1991 |
| JP | 4-144696 | 5/1992 |
| JP | H07-69922 | 8/1993 |
| JP | H08-231588 | 3/1995 |
| JP | 8-269088 | 10/1996 |
| WO | WO 01/68115 | 9/2001 |
| WO | WO 01/81368 | 11/2001 |
| WO | WO02062973 * | 8/2002 |

OTHER PUBLICATIONS

Fahmi et al. "Production of angiotensin I converting enzyme inhibitory peptides from sea bream scales," Process Biochem., 2004, 39, 1195-1200.*
Matsui "Production of hypotensive peptide, SVY, from 7S globulin of soybean protein and it physiological functions," Daizu Tanpakushitsu Kenkyu, 2003, 6, 73-77.*
Skeggs et al. "Kinetics of the reaction of renin with nine synthetic peptide substrates," Journal of Experimental Medicine, 1968, 128, 13-34.*
Official Action dated Nov. 5, 2009issued in European Application No. 04 721 339.2.
Nakano et al., "Antihypertensive Effect of Angiotensin I-Converting Enzyme Inhibitory Peptides from a Sesame Protein Hydrolysate in Spontaneously Hypertensive Rats," BioSci. Biotechnol. Biochem. vol. 70, May 2006, pp. 1118-1126.
Ohno et al., "Antihypertensive Effect of Sesame Peptide," *Gekkan Fudo Kemikaru* (*Food Chemicals*), vol. 18, No. 3 2002, pp. 11-15 [English Translation].

* cited by examiner

*Primary Examiner*—Christina Bradley
(74) *Attorney, Agent, or Firm*—Drinker Biddle & Reath LLP

(57) ABSTRACT

It is intended to provide ACE inhibitory tripeptides which are not easily digested by digestive enzymes after being orally taken and thus have fewer tendencies to lose their ACE inhibitory activity in vivo. More specifically, 3 tripeptides having an ACE inhibitory activity and showing a hypotensive effect in an animal experiment are discovered from a thermolysin digestion product of sesame. These tripeptides respectively have amino acid sequences Leu-Ser-Ala, Val-Ile-Tyr and Leu-Val-Tyr and show an angiotensin converting enzyme inhibitory activity.

9 Claims, 1 Drawing Sheet

US 7,833,985 B2

ANGIOTENSIN-CONVERTING ENZYME INHIBITORY PEPTIDES

FIELD OF THE INVENTION

This invention relates to peptides which inhibit angiotensin converting enzyme and which are therefore useful as ingredients of health foods, drugs, etc. having a hypotensive effect.

PRIOR ART

The number of patients with hypertension, which is a typical example of life-style related diseases, is increasing year by year. It is known that hypertension induces various complications such as cerebral hemorrhage, subarachnoid hemorrhage, cerebral infarction, myocardial infarction, angina, nephrosclerosis and so on. Thus, various studies have been made on the onset mechanism of hypertension.

As blood pressure-regulatory systems, the renin-angiotensin system relating to the elevation of blood pressure and the kallikrein-kinin system relating to the reduction of blood pressure play important roles. In the renin-angiotensin system, angiotensinogen secreted from the liver is converted into angiotensin I by renin produced in the kidney. Angiotensin I is further converted into angiotensin II by angiotensin converting enzyme (ACE). Angiotensin II induces contraction of smooth vascular muscles and thus elevates blood pressure. On the other hand, kallikrein in the hypotensive system acts on kininogen and thus produces bradykinin. Bradykinin has a vasodilating effect and lowers blood pressure. However, ACE has an effect of degrading bradykinin. That is to say, it is known that ACE participates in the elevation of blood pressure through the above-described two effects, i.e., producing angiotensin II which is a vasopressor peptide and inactivating bradykinin which is a hypotensive peptide. Therefore, it will be possible to reduce elevation of blood pressure by suppressing the enzyme activity of ACE. Proline derivatives such as captopril and enalapril developed as ACE inhibitors have been widely employed in treating hypertension.

In recent years, it has been reported that peptides obtained by digesting food materials with enzymes have an ACE inhibitory activity. For example, there have been reported a large number of such digestion products, e.g., a collagenase digestion product of gelatin (Japanese Patent Public Disclosure SHO 52-148631), a trypsin digestion product of casein (Japanese Patent Public Disclosure SHO 58-109425, Japanese Patent Public Disclosure SHO 59-44323, Japanese Patent Public Disclosure SHO 60-23086, Japanese Patent Public Disclosure SHO 60-23087, Japanese Patent Public Disclosure SHO 61-36226 and Japanese Patent Public Disclosure SHO 61-36227), a thermolysin digestion product of γ-zein (Japanese Patent Public Disclosure SHO 2-32127), a pepsin digestion product of sardine muscle (Japanese Patent Public Disclosure HEI 3-11097), a thermolysin digestion product of dried bonito (Japanese Patent Public Disclosure HEI 4-144696), a thermolysin digestion product of sesame protein (Japanese Patent Public Disclosure HEI 8-231588), a pepsin digestion product of κ-casein (Japanese Patent Public Disclosure 8-269088) and so on.

These ACE inhibitory peptides, being of food origin, have significant advantages, i.e., they pose few problems of safety (i.e., side effects, toxicity, etc.) and are edible like common foods. However, it has been reported that the above-described peptide products mainly comprise peptides of 5 or more amino acids (Japanese Patent Public Disclosure SHO 52-148631, Japanese Patent Public Disclosure SHO 58-109425, Japanese Patent Public Disclosure SHO 59-44323, Japanese Patent Publication SHO 60-23086, Japanese Patent Public Disclosure SHO 61-36226, Japanese Patent Public Disclosure SHO 61-36227, Japanese Patent Public Disclosure HEI 3-11097, Japanese Patent No. 3135812 and Japanese Patent Public Disclosure HEI 8-269088). It has been pointed out that peptides consisted of longer amino acid chains cannot achieve a hypotensive effect of the level expected based on the strong ACE inhibitory activity in vitro, probably because they are susceptible to digestion by digestive enzymes in the body and thus lose the ACE inhibitory activity, or, even if they remain not digested, they are not easily absorbed because of their bulky molecular structures.

SUMMARY OF THE INVENTION

Accordingly, an object of the present invention is to provide ACE inhibitory tripeptides which are not easily digested by digestive enzymes when taken orally and thus have fewer tendencies to lose their ACE inhibitory activity in vivo.

In the present invention, it is also intended to provide edible (food/drink) compositions, angiotensin converting enzyme inhibitors and hypotensive agents comprising one or more of the above-described tripeptides.

DETAILED DESCRIPTION OF THE INVENTION

Figure 1:
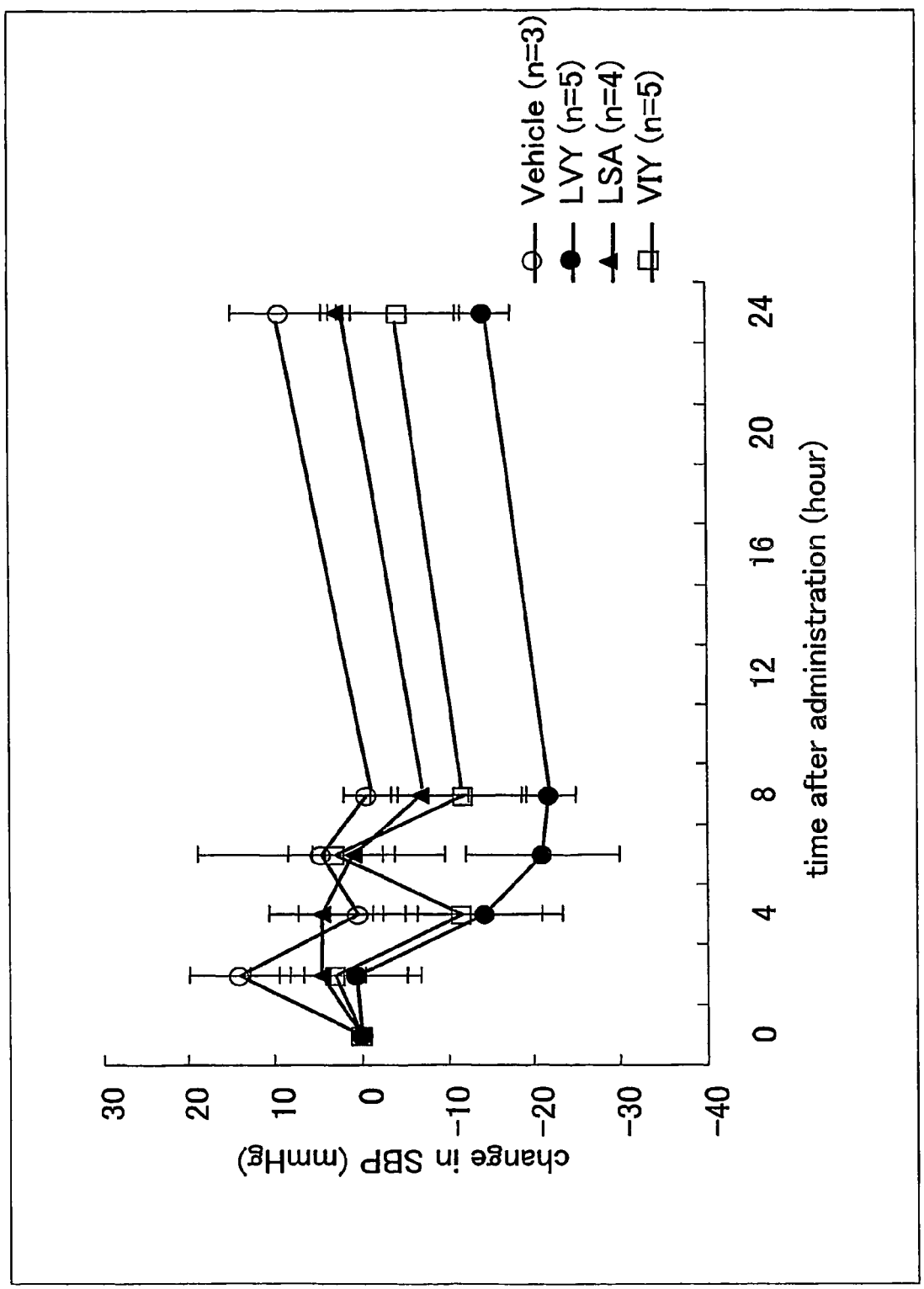
FIG. 1 is a graph showing the results of an examination on the hypotensive effects of the peptides according to the present invention with the use of spontaneous hypotensive rats.

The present inventors searched for ACE inhibitory peptides consisted of not more than 3 amino acids, assuming that thermolysin digestion products of food materials would contain peptides capable of overcoming the above-described problems. As a result, they succeeded in discovering 3 tripeptides in a thermolysin digestion product of sesame, said tripeptides having an ACE inhibitory activity and showing a hypotensive effect in an animal experiment. The present invention was accomplished based on these findings.

Accordingly, the present invention provides tripeptides respectively having the amino acid sequences Leu-Ser-Ala, Val-Ile-Tyr and Leu-Val-Tyr and showing an angiotensin converting enzyme inhibitory activity.

The present invention further provides edible compositions, angiotensin converting enzyme inhibitors and hypotensive agents containing one or more of the above-described tripeptides.

The tripeptides according to the present invention may be produced by chemical synthesis. However, in an embodiment of the invention wherein the tripeptides are added to foods, drinks or oral drugs to exploit their ACE inhibitory activity, it is preferred to produce an edible composition enriched with at least one of the above-described 3 tripeptides by digesting vegetable protein originating in sesame or the like with thermolysin and further purifying the same.

As a vegetable protein source, use can be made of protein-rich plant tissues (preferably seeds), for example, cereals such as rice, wheat, barely, oat and corn, or beans such as kidney bean, broad bean, soybean and mung bean and sesame.

When the peptides according to the invention are to be obtained by digestion with thermolysin, the treatment procedure varies depending on the properties of the starting material. It is preferred that, as a pretreatment, the material is first defatted by, for example, removing the juice by squeezing or extracting the fat with a solvent such as an alcohol, acetone, hexane, etc. To improve the efficiency of the digestion of the starting material with thermolysin, it is also preferred that the starting material be finely milled and then suspended in water under stirring. In the case of a hardly soluble protein, it is also possible to employ another pretreatment such as addition of sodium hydroxide or heating to thereby uniformly dissolve or suspend the protein. Then thermolysin is added thereto in an appropriate amount, preferably from 500 to 50000 PU per g of the protein and the protein digestion reaction is carried out at pH 5 to 9, at a temperature of 10 to 80° C., for 0.5 to 48 hours either in a stationary state or under stirring. ("PU" means "protease unit" and 1 PU is defined as the amount of an enzyme giving an increase in non-protein Folin's color equivalent to 1 μg of tyrosine per min using milk casein as the substrate at pH 7.2 and at 35° C.) To examine whether or not sufficient progress of the reaction has been made (i.e., the reaction is sufficient for obtaining the purposed tripeptides), use can be made of a method comprising "applying the liquid reaction mixture to high-performance liquid chromatography using an ODS column and determining the elution pattern by measuring the absorbance at 210 nm". The reaction is ceased by adding, for example, hydrochloric acid. Alternatively, the thermolysin may be inactivated by heating. It is also possible to cease the reaction by both the adding hydrochloric acid and heating. The liquid reaction mixture is subjected to centrifugation, filtration, etc. and the precipitate is removed. The filtrate thus obtained is neutralized with sodium hydroxide or hydrochloric acid and then concentrated. Further, off-flavor (for example, bitterness, harshness, offensive odor, etc.) can be removed if necessary by treating it with activated charcoal. The sesame peptides thus obtained contain Leu-Ser-Ala, Val-Ile-Tyr and Leu-Val-Tyr each in an amount of from 0.001% by weight to 0.1% by weight.

The thermolysin digestion product obtained in the above-described manner can be used as the tripeptide composition of the invention with or without a further treatment with an ion exchange resin, a high-porous polymer resin, etc. to remove high-molecular weight proteins, to thereby provide a partially purified product rich in the tripeptides of the present invention. These digestion product and partially purified product in general will be sometimes referred to hereinafter as "tripeptide-rich composition". Such a composition may be further treated, if necessary, by activated charcoal to remove off-flavor (for example, bitterness, harshness, offensive smell, etc.) before using.

To obtain a purified preparation of the peptides of the invention, the above-described concentrate is subjected to gel filtration column chromatography, chromatography with the use of an ion exchange resin or a high-porous polymer resin, affinity chromatography, etc. and peptide fractions of the invention having the ACE inhibitory activity are combined. Next, the combined active fractions can be purified by a method commonly employed in purifying peptides, for example, high-performance liquid chromatography with the use of a reversed phase column such as an ODS column or a C30 column to thereby provide single forms of the peptides in a substantially pure state. The tripeptides of the invention can be obtained not only from sesame (e.g., *Sesamum indicum* L.) but also from cereals such as rice (e.g., *Oryza sativa* L.), wheat (e.g., *Triticum aestivum* L., *T. durum* Desf., *T. turgidum* L., *T. pyramidale* (Delile) Perciv. non Delile ex Schult, *T. abyssinicum* Vavilov, and *T. carthlicum* Nevski), barley (e.g., *Hordeum vulgare* L.), oat (e.g., *Avena sativa* L.) or corn (e.g., *Zea mays* L.), or beans such as kidney bean (e.g., *Phaseolus vulgaris* L.), broad bean (e.g., *Vicia faba* L.), soybean (e.g., *Glycine max* (L.) Merrill) or mung bean (e.g., *Vigna radiata* (L.) R. Wilcz.) by the method as described above. The ACE inhibitory activity of the tripeptides or tripeptide-rich compositions can be measured by, for example, an in vitro test method and/or an in vivo test method as will be described in Examples hereinafter.

When each peptide of the invention is prepared by chemical synthesis, the synthesis can be carried out by any of the solid phase method and the liquid phase method conventionally employed in synthesizing a peptide. The peptide of the invention obtained by the synthesis can be purified by a purification procedure commonly employed, for example, reverse phase high-performance liquid chromatography, chromatography with the use of an ion exchange resin or a high-porous polymer resin, affinity chromatography, etc.

The tripeptides thus obtained and the composition enriched with the tripeptides have a strong activity of inhibiting ACE and exhibit the strong ACE inhibitory effect when they are taken orally. Therefore, they are useful as highly potent ACE inhibitors. Moreover, they are easily absorbed via the gastrointestinal tract and are relatively stable under heat. Due to these characteristics, they are also applicable to foods, drinks and medicinal preparations in various forms.

Accordingly, the present invention provides an edible composition which comprises one or more of the above-described tripeptides and which is expected to have an angiotensin converting enzyme inhibitory effect, an angiotensin converting enzyme inhibitor and a hypotensive agent containing one or more of the above-described tripeptides.

In a case where one or more of the tripeptides of the invention are used in foods, drinks, drugs, etc., use may be made of a tripeptide sufficiently purified from the thermolysin digestion product of the protein fraction of sesame, etc., or use may be made of a chemically synthesized product. Alternatively, since the tripeptides of the invention have a high stability and a strong ACE inhibitory activity, the above-described partially purified product or the thermolysin digestion product or the partially purified product thereof may be used as such as a tripeptide-rich composition; in such a case also, a sufficient ACE inhibitory activity will be obtained, and hence, this is a preferred embodiment of the invention.

The edible composition according to the present invention is produced by adding one or more of the above-described tripeptides in an amount of from 0.001 mg to 100 mg, preferably from 0.01 mg to 20 mg and still preferably from 0.1 mg to 10 mg in a single intake dose. The tripeptides of the invention are in the form of a solid or a powder which can be easily handled and are highly soluble in water. Also, the tripeptides can be well absorbed via the gastrointestinal tract. Therefore, the tripeptides may be added to foods at any stage by any method without particular restriction. That is to say, the tripeptides can be added in the form of a powder, a solution, a suspension, etc. at the starting stage, the intermediate stage or the final stage of a food production process by using a method commonly employed in the field of food industry. Temporary, intermittent, continuous or daily intake of the edible composition containing the tripeptides of the invention makes it possible to inhibit angiotensin converting enzyme and obtain, for example, a hypotensive effect. The foods and drinks may be in the form of, for example, a solid, a semifluid or a fluid. Examples of solid foods include general foods and health foods in the forms of biscuits, sheets, pills such as tablets and capsules, granules, powders and so on. Examples of semifluid foods include products in the forms of pastes, jellies, gels and so on. Examples of fluid foods include general drink products and health drinks in the forms of juices, cold drinks, tea drinks, tonic drinks and so on. Such foods or drinks may be supplied in the form of a nutrition supplemental drink or a seasoning to enable us to continuously take the tripeptides of the invention, thereby suppressing the risk of blood pressure elevation.

The medicinal composition of the invention contains the tripeptides of the invention in an amount similar to the edible composition as described above. The medicinal composition of the invention can be temporarily administered to a hypertensive patient to suppress the angiotensin converting enzyme in the body and thereby to obtain a hypotensive effect. Alternatively, the medicinal composition of the invention can be continuously administered safely, since the active ingredient originates in a natural material. As an example of the diseases which can be treated and/or prevented by the medicinal composition of the invention, hypertension can be mentioned. It is preferable that the medicinal composition is in the form of an oral preparation such as tablets, capsules, dusts, granules or syrups. Examples of preparations for parenteral administration include aseptic solutions to be administered intravenously, intraarterially, subcutaneously, intramuscularly or intranasally. Such a solution may be in the form of a dry solid which is to be dissolved before using. An injection preparation can be produced by dissolving an effective amount of the tripeptide in physiological saline and treating under aseptic conditions as commonly employed in producing injection preparations.

EXAMPLES

Now, the present invention will be described in greater detail by reference to the following Examples.

Method of Measuring ACE Inhibitory Activity

In the present invention, the ACE inhibitory activity ($IC_{50}$) was measured in accordance with the following method.

| | |
|---|---|
| Buffer: | 0.1 M HEPES, 0.3 M NaCl, 0.01% Triton-X (pH 8.3). |
| Enzyme: | ACE from rabbit lung (Sigma). Dissolved in the above buffer and adjusted to a concentration of 1 mU/50 μl. |
| Substrate: | Bz-Gly-His-Leu*$H_2O$ (Peptide Institute Inc.). 8.95 mg of the substrate was dissolved in 1 ml of dimethyl sulfoxide and further diluted 5-fold with water (final concentration: 4 mM). |

5 μl of a sample containing the peptide of the invention was pipetted into a 96-well microplate. After adding 25 μl of the buffer and 10 μl of the enzyme, the mixture was thoroughly stirred and incubated at 37° C. for 5 minutes. After adding 10 μl of the substrate, the mixture was reacted at 37° C. for 30 minutes. Then the reaction was ceased by adding 40 μl of 0.1 N NaOH. After adding 20 μl of a methanol solution of 1% o-phthalaldehyde and allowing to stand at room temperature for 10 minutes, 100 μl of 0.1 N HCl was added and the resultant mixture was incubated at 37° C. for 30 minutes. Then the amount of His-Leu formed by the hydrolysis by ACE was determined by exciting (at 355 nm) the fluorescent substance formed by the reaction between the amino group in the histidine residue and o-phthalaldehyde and measuring the fluorescence wavelength at 460 nm. Then the percentage inhibition by the peptide of the invention was determined in accordance with the following equation and the ACE inhibitory activity ($IC_{50}$) was calculated.

Percentage inhibition=$\{1-(A-a)/(B-b)\} \times 100$

A: Measurement of fluorescence when the sample was added.
a: Measurement of fluorescence when the sample was added and the buffer was added as a substitute for the enzyme.
B: Measurement of fluorescence when distilled water was added as a substitute for the sample.
b: Measurement of fluorescence when distilled water was added as a substitute for the sample and the buffer was added as a substitute for the enzyme.

Example 1

Production and Purification of Peptide

2 L of water was added to 100 g of defatted sesame and the pH value of the resultant mixture was adjusted to 12.0 to 12.5 by adding NaOH. After stirring at 55° C. for 1 hour, the mixture was filtered to give a protein extract. HCl was added to the protein extract to adjust the pH value to 4.0. After centrifuging, sesame protein (weight on dry basis: 19.8 g) was obtained.

To 10 g of the obtained sesame protein, 300 ml of water was added and the pH value of the mixture was adjusted to 7.5 with NaOH. Then 10 mg of thermolysin (Nacalai Tesque, 7000 PU/mg) was added thereto and the mixture was reacted under gentle stirring at 65° C. for 6 hours. After the completion of the reaction, HCl was added to the reaction mixture to adjust to pH 4.0 and the thermolysin was inactivated by heating to 90° C. for 10 minutes. After heating, the thus formed precipitate was removed by centrifugation and the supernatant was filtered through paper filter (Toyo, No. 2). The filtrate was freeze-dried to give 5.9 g of a peptide powder.

80 mg of this peptide powder was dissolved in 2 ml of 10% ethanol solution and subjected to gel filtration column chromatography. The conditions employed were as follows.

| | |
|---|---|
| Column: | Bio-Gel P-2 (15 mm ID × 820 mm L, Bio-Rad). |
| Eluent: | 10% ethanol. |
| Flow rate: | 0.15 ml/min. |
| Detection: | UV 210 nm. |

The eluate from the column was collected in fractions at intervals of 15 minutes with the use of a fraction collector. The ACE inhibitory activity of each fraction was measured in accordance with the method described above. As a result, the major ACE inhibitory activity under the above conditions was observed in fractions 32 to 38. These fractions were combined and freeze-dried. This procedure was repeated three times and thus 37.5 mg of peptides was obtained in total.

Next, 37.5 mg of the ACE inhibitory active peptides obtained by the Bio-Gel P-2 gel filtration column chromatography was dissolved in 2 ml of purified water and subjected to high-performance liquid chromatography with the use of an ODS column to thereby fractionate the peptides. The conditions employed were as follows.

| | |
|---|---|
| Column: | Develosil ODS-10 (20 mm ID × 250 mm L, Nomura Chemical). |
| Mobile phase: | Buffer A: 5% $CH_3CN$, 0.1% TFA.<br>Buffer B: 40% $CH_3CN$, 0.1% TFA. |
| Gradient: | 0 to 20 min: 0% Buffer B<br>20 to 80 min: 0 to 100% Buffer B. |
| Flow rate: | 10 ml/min. |
| Detection: | UV 210 nm. |

Under the above conditions, the eluate was collected in fractions at intervals of 1 minute with the use of a fraction collector. A 5 µl portion of each fraction was pipetted into a 96-well microplate and evaporated to dryness under reduced pressure. Next, the residue was dissolved in 5 µl of purified water to give a sample for measuring the ACE inhibitory activity. Then the ACE inhibitory activity of each fraction was measured in accordance with the method described above. As a result, fractions 39, 52 and 54 showed strong ACE inhibitory activities. The 3 fractions were freeze-dried and thus a small amount of peptides was obtained from each fraction.

Purification of ACE Inhibitory Peptide in Fraction 39

The freeze-dried peptide of fraction 39 was dissolved in 200 µl of purified water and subjected to high-performance liquid chromatography with the use of a C30 column to thereby fractionate the peptides. The conditions employed were as follows.

| | |
|---|---|
| Column: | Develosil C30-UG-5 (10 mm ID × 250 mm L, Nomura Chemical). |
| Mobile phase: | Buffer: 10% $CH_3CN$, 0.1% TFA. |
| Flow rate: | 4 ml/min. |
| Detection: | UV 210 nm. |

Under the above conditions, the eluate was collected in fractions at intervals of 15 seconds with the use of a fraction collector. A 5 µl portion of each fraction was pipetted into a 96-well microplate and evaporated to dryness under reduced pressure. Next, the residue was dissolved in 5 µl of purified water to give a sample for measuring the ACE inhibitory activity. Then the ACE inhibitory activity of each fraction was measured in accordance with the method described above. As a result, fractions 44 and 45 showed strong ACE inhibitory activities. The 2 fractions were freeze-dried separately and thus a small amount of peptide was obtained from each fraction. Next, these fractions were subjected to amino acid analysis and TOF MS/MS analysis. As a result, it was found that the peptide of fractions 44 and 45 was Leu-Ser-Ala.

Purification of ACE Inhibitory Peptide in Fraction 52

The freeze-dried peptide of fraction 52 was dissolved in 200 µl of purified water and subjected to high-performance liquid chromatography with the use of a C30 column to thereby fractionate the peptides. The conditions employed were as follows.

| | |
|---|---|
| Column: | Develosil C30-UG-5 (10 mm ID × 250 mm L) |
| Mobile phase: | Buffer: 14% $CH_3CN$, 0.1% TFA. |
| Flow rate: | 4 ml/min. |
| Detection: | UV 210 nm. |

Under the above conditions, the eluate was collected in fractions at intervals of 15 seconds with the use of a fraction collector. A 5 µl portion of each fraction was pipetted into a 96-well microplate and evaporated to dryness under reduced pressure. Next, the residue was dissolved in 5 µl of purified water to give a sample for measuring the ACE inhibitory activity. Then the ACE inhibitory activity of each fraction was measured in accordance with the method described above. As a result, fractions 89 and 90 and fractions 96 and 97 showed strong ACE inhibitory activities. The 4 fractions were freeze-dried separately and thus a small amount of peptide was obtained from each fraction. Next, these fractions were subjected to amino acid analysis and TOF MS/MS analysis. As a result, it was found that the peptide of fractions 89 and 90 was Ile-Val-Tyr, while the peptide of fractions 96 and 97 was Val-Ile-Tyr.

Purification of ACE Inhibitory Peptide in Fraction 54

The freeze-dried peptide of fraction 54 was dissolved in 200 µl of purified water and subjected to high-performance liquid chromatography with the use of a C30 column to thereby fractionate the peptides. The conditions employed were as follows.

| | |
|---|---|
| Column: | Develosil C30-UG-5 (10 mm ID × 250 mm L, Nomura Chemical). |
| Mobile phase: | Buffer: 17% $CH_3CN$, 0.1% TFA. |
| Flow rate: | 4 ml/min. |
| Detection: | UV 210 nm. |

Under the above conditions, the eluate was collected in fractions at intervals of 15 seconds with the use of a fraction collector. A 5 µl portion of each fraction was pipetted into a 96-well microplate and evaporated to dryness under reduced pressure. Next, the residue was dissolved in 5 µl of purified water to give a sample for measuring the ACE inhibitory activity. Then the ACE inhibitory activity of each fraction was measured in accordance with the method described above. As a result, fractions 69 to 73 showed strong ACE inhibitory activities. The 5 fractions were separately freeze-dried and thus a small amount of peptide was obtained from each fraction. Next, fractions 69, 70, 72 and 73 among them were subjected to amino acid analysis and TOF MS/MS analysis. As a result, it was found that the peptide of each of these fractions was Leu-Val-Tyr.

Example 2

Production of Peptides by Chemical Synthesis

Using an automatic peptide synthesizer (Model ABI 430) manufactured by Applied Biosystems, a purposed protected peptide resin was synthesized by starting with the C-terminus and extending the peptide chain successively by the BOC method in accordance with the program.

After the completion of the construction of the peptide on the resin, the protected peptide resin was dried. The protected peptide thus obtained was deprotected and the peptide was removed from the resin support by treating it with anhydrous hydrogen fluoride (HF/p-Cresol 8:2 v/v, 60 minutes). The crude peptide thus obtained was extracted with 90% acetic acid and then freeze-dried to give a powdery solid. The crude peptide thus obtained was further purified by high-performance liquid chromatography with the use of an ODS column and thus the purposed peptide was obtained.

| | |
|---|---|
| Column: | YMC-Pack ODS-2 (30 mm ID × 250 mm L, YMC). |
| Mobile phase: | Buffer A: 5% $CH_3CN$, 0.1% TFA. |
| | Buffer B: 40% $CH_3CN$, 0.1% TFA. |
| Gradient: | 0 to 10 min: 0% Buffer B |
| | 10 to 90 min: 0 to 100% Buffer B. |
| Flow rate: | 20 ml/min. |
| Detection: | UV 220 nm. |

The purity of the peptide thus purified was examined by high-performance liquid chromatography with the use of an ODS column.

| Column: | Zorbax 300SB-C18 (4.6 mm ID × 150 mm L, Agilent Technologies). |
|---|---|
| Mobile phase: | Buffer A: 1% CH$_3$CN, 0.1% TFA. Buffer B: 60% CH$_3$CN, 0.1% TFA. |
| Gradient: | 0 to 25 min: 0 to 100% Buffer B |
| Flow rate: | 1 ml/min. |
| Detection: | UV 220 nm. |

Synthesis of Leu-Ser-Ala

Using Boc-Ala (BrZ) resin (0.5 mmol) as the starting amino acid resin support, the peptide chain was extended with the use of 2 mM portions of amino acid derivatives Boc-Ser and Boc-Leu. Then purified Leu-Ser-Ala was obtained by the purification method described above in Example 2. The purity of the purified product measured by the method described above in Example 2 was 99.0%.

Synthesis of Val-Ile-Tyr

Using Boc-Tyr (BrZ) resin (0.5 mmol) as the starting amino acid resin support, a peptide chain was extended with the use of 2 mM portions of amino acid derivatives Boc-Ile and Boc-Val. Then purified Val-Ile-Tyr was obtained by the purification method described above in Example 2. The purity of the purified product measured by the method described above in Example 2 was 98.8%.

Synthesis of Leu-Val-Tyr

Using Boc-Tyr (BrZ) resin (0.5 mmol) as the starting amino acid resin support, a peptide chain was extended with the use of 2 mM portions of amino acid derivatives Boc-Val and Boc-Leu. Then purified Leu-Val-Tyr was obtained by the purification method described above in Example 2. The purity of the purified product measured by the method described above in Example 2 was 99.2%.

Example 3

Measurement of ACE Inhibitory Activity of Peptide

The ACE inhibitory activities of the 3 peptides obtained in Example 2 were measured in accordance with the method described above and IC$_{50}$ values were determined. Table 1 shows the results. As a control, the ACE inhibitory activity of the sesame peptide powder obtained in Example 1 was also measured and the IC$_{50}$ value thereof was determined.

TABLE 1

| Peptide | Inhibitory activity (IC$_{50}$) | |
|---|---|---|
| | μg/ml | μM |
| Leu-Ser-Ala | 2.4 | 8.4 |
| Val-Ile-Tyr | 1.6 | 4.2 |
| Leu-Val-Tyr | 0.84 | 2.1 |
| Peptide powder | — | 50.3 |

Example 4

Hypotensive Effect of Peptide on Spontaneous Hypertensive Rat

SHR rats aged 17 to 22 weeks were fasted overnight. Then each of the 3 peptides obtained in Example 2 was orally administered in a dose of 1 mg/kg. To a control group, the same amount of water was orally administered for comparison. Before, and until 24 hours after the administration, changes in systolic blood pressure were measured (BP-98A, SOFTRON). FIG. 1 shows the results.

Example 5

Using the synthetic products of Example 2, a cereal tea drink was produced from the following ingredients.

Composition:

| roasted barley | 60 g |
|---|---|
| hot water | 2000 ml |

Peptides of Example 2

| Leu-Ser-Ala | 19 mg |
|---|---|
| Val-Ile-Tyr | 18 mg |
| Leu-Val-Tyr | 18 mg |

Production Method:

Hot water was added to roasted barley and heated to 90° C. for 5 minutes. After cooling to 40° C., the mixture was filtered. Then water was added to the extract to adjust the volume to 2000 ml. Next, the above peptides were added and dissolved by stirring to give a cereal tea drink.

Example 6

Isolation and Quantitation of Leu-Val-Tyr from Proteinase Treated Plant Seeds

Rice and oat grains were respectively weighed at 25 g, which were then ground to provide powders. 50 ml of hexane was added to each flower and the solvent was removed through a filter paper (Whattman, No. 1). The same hexane treatment was repeated 4 times in total. Hexane was removed from the residue on the filter paper to provide 18.8 g of a defatted rice powder and 15.9 g of a defatted oat powder, respectively.

Each of the defatted flour was weighed at 10 g, suspended in 200 ml of 0.01 N NaOH and stirred at 55° C. for 1 hour. After cooling to room temperature, the suspension was filtered through a filter paper (Whattman, No. 1). The filtrate was adjusted to pH 4.0 by an addition of 0.1 N HCl. The precipitate thus formed was collected by centrifugation, freeze-dried to yield 0.38 g and 0.57 g of crude protein powders of rice and oat, respectively.

The obtained powder was weighed at 0.2 g, suspended in 10 ml of 0.1 mM CaCl$_2$. The suspension was adjusted to pH 7.5, and 0.2 mg of thermolysin (7,000 PU/mg, Nacalai Tesque) was added thereto to effect the enzyme reaction under gentle mixing at 65° C. for 6 hours. After the reaction period, pH was adjusted to 4.0 by 1 N HCl and the thermolysin was inactivated by heating the mixture at 90° C. for 10 minutes. The precipitate formed by the heating was removed by centrifugation at 3,000 rpm for 30 minutes. The supernatant was freeze dried to provide peptide powders of 28.6 mg from rice and 87.8 mg from oat.

Isolation and quantitation of Leu-Val-Tyr, as one of the peptides of the invention, from the rice and the oat peptide powders obtained above was carried out as follows.

i) Pre-Treatment on PD-10 Column

Each of the peptide powders of rice and oat was weighed at 20 mg, dissolved in 0.1 N acetic acid to be 5 mg/ml, filtered through a micro-filter (Millex-HV, pore size 0.45 µm, filter diameter 13 mm, Millipore Corporation) to remove insoluble components. A 2.5 ml portion of the filtrate was introduced into a PD-10 column (desalting column, Amersham Biosciences) equilibrated with 0.1 N acetic acid. The column was washed with a further 3.5 ml volume of 0.1 N acetic acid. Then the fraction eluted with an additional 3.0 ml volume of 0.1 N acetic acid was collected, evaporated to dryness, dissolved in 0.5 ml of water and then freeze-dried.

ii) Gel Filtration HPLC with the Use of TSK-GEL G2000SWXL

The specimen prepared by the pre-treatment on the PD-10 column was dissolved in 250 µl of 45% $CH_3CN$, 0.1% TFA to be centrifuged at 2,000 rpm for 5 minutes. The filtrate was filtered through a micro-filter (Millex-HV, pore size 0.45 µm, filter diameter 13 mm, Millipore Corporation) to remove insoluble components.

A 50 µl portion of the filtrate was charged to a column of TSK-GEL G2000SWXL (7.8×300 mm, Tosoh Corporation) equilibrated with 45% $CH_3CN$, 0.1% TFA, and HPLC was performed with 45% $CH_3CN$, 0.1% TFA (flow rate 0.7 ml/min., detection wavelength 280 nm). The eluate of 1 minute between 30 seconds before and after the retention time was collected, evaporated to dryness, dissolved in 0.5 ml of water and freeze-dried. The retention time of Leu-Val-Tyr was pre-determined by separately subjecting synthetic Leu-Val-Tyr to HPLC under the same conditions.

iii) Reverse HPLC on Develosil C30-UG-5 (Quantitation of Leu-Val-Tyr)

Leu-Val-Tyr in the active peptide fractions from the gel filtration was quantitatively analyzed by reverse HPLC on a Develosil C30-UG-5 column (3×150 mm, Nomura Chemical Co., Ltd.). The fraction from the gel filtration HPLC on TSK-GEL G2000SWXL was dissolved in 250 µl of 5% $CH_3CN$, 0.1% TFA, centrifuged at 2,000 rpm for 5 minutes, and the supernatant was filtered through a micro-filter (Millex-HV, pore size 0.45 µm, filter diameter 13 mm, Millipore Corporation) to remove insoluble components. A 50 µl portion of the filtrate was charged on a Develosil C30-UG-5 column equilibrated with 5% $CH_3CN$, 0.1% TFA to perform a chromatography under the following conditions:

| Elution solvent | |
| --- | --- |
| 0-5 min.: | 5% $CH_3CN$, 0.1% TFA |
| 5-10 min.: | 5-14% $CH_3CN$, 0.1% TFA |
| 10-35 min.: | 14% $CH_3CN$, 0.1% TFA |
| Flow rate: | 0.4 ml |
| Detection wavelength: | 280 nm |

The peak of the each peptide of rice and oat in the Develosil C30-UG-5 column chromatography, of which the retention time corresponded to that of the authentic Leu-Val-Tyr of the peptide, was collected. The fraction was subjected to a TOF MS analysis and a TOF MS/MS analysis to confirm that the fraction was Leu-Val-Tyr.

A calibration curve was prepared by charging different amounts of the authentic Leu-Val-Tyr to the same Develosil C30-UG-5 column under the same conditions as described above and plotting the peak areas against the charged amounts.

Calibration Curve $Y=249197X-2150.6 (R^2=0.9991)$

Y: peak area, X: amount of Leu-Val-Tyr (µg)

The peak areas of the Leu-Val-Tyr fractions from the Develosil C30-UG-5 chromatography of rice and oat were applied to the calibration curve. As a result, the amounts of Leu-Val-Tyr in 1 mg of the peptide from rice and oat were determined to be 0.71 µg and 1.05 µg, respectively.

The invention claimed is:

1. A purified tripeptide consisting of an amino acid sequence selected from the group consisting of Leu-Ser-Ala and Val-Ile-Tyr.

2. An edible composition containing one or more purified tripeptides consisting of an amino acid sequence selected from the group consisting of Leu-Ser-Ala and Val-Ile-Tyr.

3. An edible composition according to claim 2 comprising from 0.001 mg to 100 mg of said tripeptides in a single intake dose.

4. An angiotensin converting enzyme inhibitor comprising from 0.001 mg to 100 mg of a purified tripeptide consisting of an amino acid sequence selected from the group consisting of Leu-Ser-Ala and Val-Ile-Tyr in a single dose for oral administration.

5. A hypotensive agent comprising from 0.001 mg to 100 mg of a purified tripeptide consisting of an amino acid sequence selected from the group consisting of Leu-Ser-Ala and Val-Ile-Tyr in a single dose for oral administration.

6. A method for treating hypertension, wherein the method comprises administering one or more tripeptides of claim 1.

7. A method for inhibiting an angiotensin converting enzyme, wherein the method comprises allowing one or more tripeptides of claim 1 to act on the enzyme.

8. A method for suppressing elevation of blood pressure, wherein the method comprises administering one or more tripeptides of claim 1.

9. A method for reducing blood pressure, wherein the method comprises administering one or more tripeptides of claim 1.

* * * * *